(12) United States Patent
Yerazunis et al.

(10) Patent No.: US 7,008,795 B2
(45) Date of Patent: Mar. 7, 2006

(54) MULTI-WAY LED-BASED CHEMOCHROMIC SENSOR

(75) Inventors: William S. Yerazunis, Acton, MA (US); Dermot Diamond, Coolquoy (IE); Paul H. Dietz, Hopkinton, MA (US)

(73) Assignee: Mitsubishi Electric Research Labs, Inc., Cambridge, MA (US)

( * ) Notice: Subject to any disclaimer, the term of this patent is extended or adjusted under 35 U.S.C. 154(b) by 478 days.

(21) Appl. No.: 10/251,251

(22) Filed: Sep. 20, 2002

(65) Prior Publication Data

US 2004/0057873 A1 Mar. 25, 2004

(51) Int. Cl.
*G01N 21/78* (2006.01)
(52) U.S. Cl. .................. 436/164; 436/169; 422/82.05; 422/82.09; 422/91
(58) Field of Classification Search ................ 436/167, 436/169, 170, 172; 422/82.05, 82.08, 82.09, 422/82.11, 86, 87, 91
See application file for complete search history.

(56) References Cited

U.S. PATENT DOCUMENTS

| | | | | |
|---|---|---|---|---|
| 4,848,901 | A | * | 7/1989 | Hood, Jr. ..................... 356/41 |
| 5,149,962 | A | * | 9/1992 | Maurice ................. 250/227.17 |
| 5,177,352 | A | * | 1/1993 | Carson et al. .............. 250/221 |
| 5,408,092 | A | * | 4/1995 | Maurice et al. ......... 250/227.21 |

OTHER PUBLICATIONS

Benson et al., "Low-cost fiber-optic chemochromic hydrogen gas detector," Proceedings of the 1999 U. S. DOE Hydrogen Program Review, 1999.

* cited by examiner

*Primary Examiner*—Jeffrey R. Snay
(74) *Attorney, Agent, or Firm*—Dirk Brinkman; Andrew J. Curtin

(57) ABSTRACT

A chemochromic sensor includes multiple bi-directional LEDs, each optically aligned with one or more test areas. Each LED is used as both a light emitter when driven in forward bias, and as a light detector when driven in reverse bias. By alternating the bias on the LEDs, multi-way light measurements of the test area can be obtained.

9 Claims, 3 Drawing Sheets

MULTI-WAY LED-BASED CHEMOCHROMIC SENSOR

FIELD OF THE INVENTION

This invention relates generally to chemochromic sensors, and more particularly to LED-based chemochromic sensors.

BACKGROUND OF THE INVENTION

In a chemochromic sensor, a test material is allowed to react with a chemochromic reagent in a test area. A catalyst can be used to facilitate a reversible reaction. The reaction changes the optical property of the reagent, which can be measured with a light sensor.

Prior art chemochromic sensors typically use one-way light measurements of the test area. Light is generated by a light-emitting diode (LED) and sensed by a phototransistor, see, e.g., Benson et al., "Low-cost fiber-optic chemochromic hydrogen gas detector," Proceedings 1999 U.S. DOE Hydrogen Program review, NREL/CP-570-26938, 1999.

Because the prior art uses one-way light measurements, calibration of the sensor with known quantities of the test material is necessary, and aging characteristics of the chemochromic reagent must also be known. Therefore, it is desired to provide a chemochromic sensor that uses nulling and differential measurements.

SUMMARY OF THE INVENTION

The present invention provides a multi-way LED-based chemochromic sensor. The sensor uses multiple bi-directional LEDs, each LED is optically aligned with one or more test areas. Each LED is used as both a light emitter when driven in forward bias, and as a light detector when driven in reverse bias. By alternating the bias on the LEDs, multi-way light measurements of the test area can be obtained.

DETAILED DESCRIPTION OF THE PREFERRED EMBODIMENT

Figure 1:
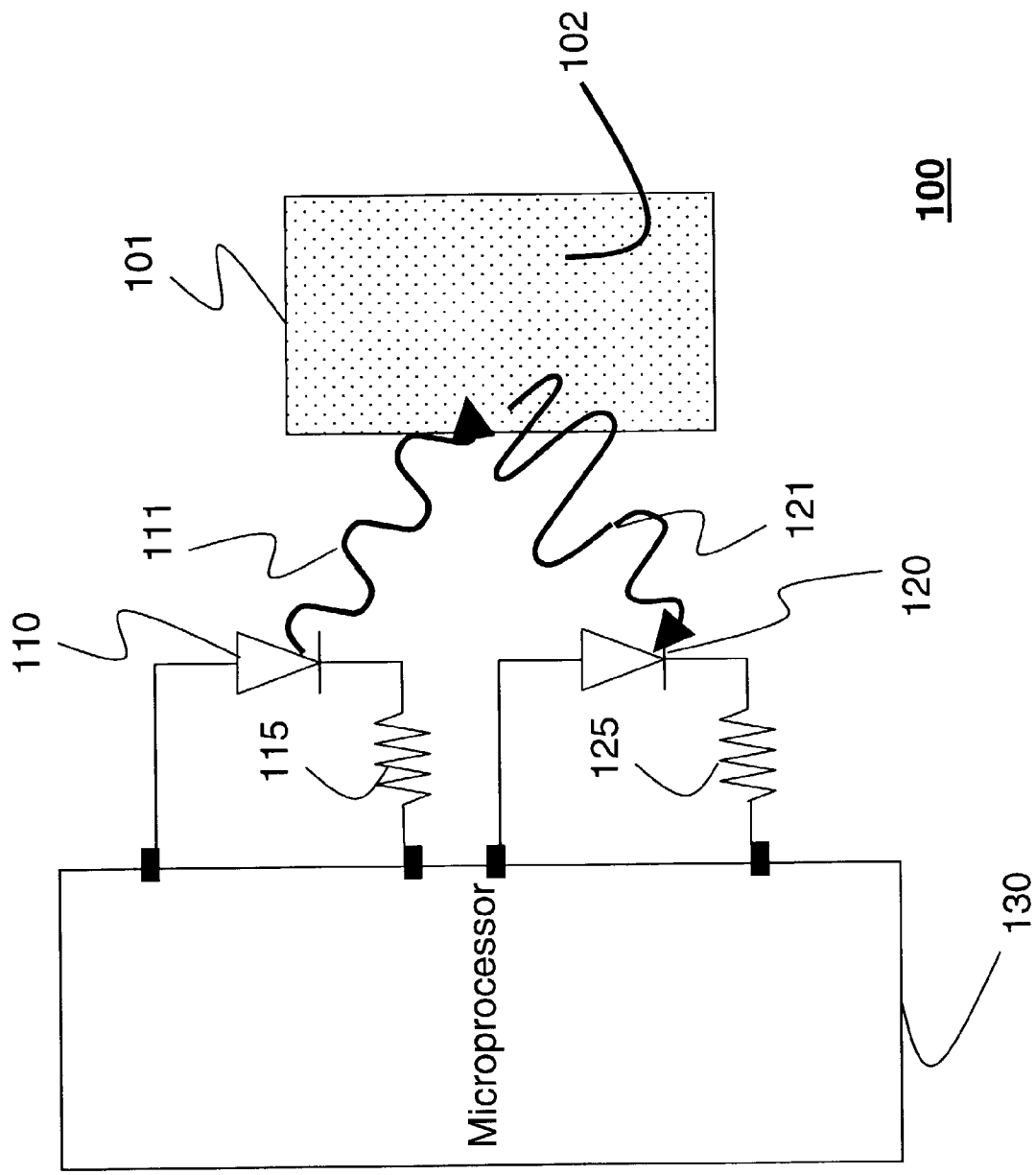
FIG. 1 is a block diagram of a multi-way LED-based chemochromic sensor according to the invention.

FIG. 1 shows a multi-way LED-based chemochromic sensor 100 according to the invention. A first bi-directional LED 110 and a second bi-directional LED 120 are connected respectively in series to pairs of I/O pins of a microprocessor 130 via resistors 115 and 125. The bias on the LEDs determines whether the LEDs emit or sense light. For a detailed description of light emitting diodes operating as both an emitter and a sensor see U.S. patent application Ser No. 10/126,761 "Communication Using Bi-Directional LEDs," filed by Dietz et al. on Apr. 19, 2002, incorporated herein by reference in its entirety.

For the LED to operate as a sensor, a junction capacitance of a reverse-biased LED is first charged. The junction is then exposed to light, which causes the junction voltage to drop from a logic-high level to a logic-low level. The amount of time that it takes to effect this drop is a measure of the amount of incident light, and in this application the amount of test material. The amount of background light to subtract can be measured by turning the emitting LED off.

A test area 101 is exposed to a mixture 102 of a chemochromic reagent and a test material, generally in combination or alone "chemochromic materials." The mixture, in liquid or gas form, can be applied to the test area in any number of known manners. The mixture 102 is illuminated 111 by the first LED 110 when it is driven in forward bias. Reflected light 121 is sensed by the second LED 120 when it is driven in reverse bias. The amount of sensed light is measured by the microprocessor 130 executing operating and application programs. The microprocessor also determines the bias on the LEDs. By reversing the bias, light can be emitted by the LED 120, and sensed by the LED 110 to provide a multi-way LED-based chemochromic sensor. By measuring the amount of light in both directions, and comparing the two measurements nulling and differential measurements can be obtained.

Figure 2:
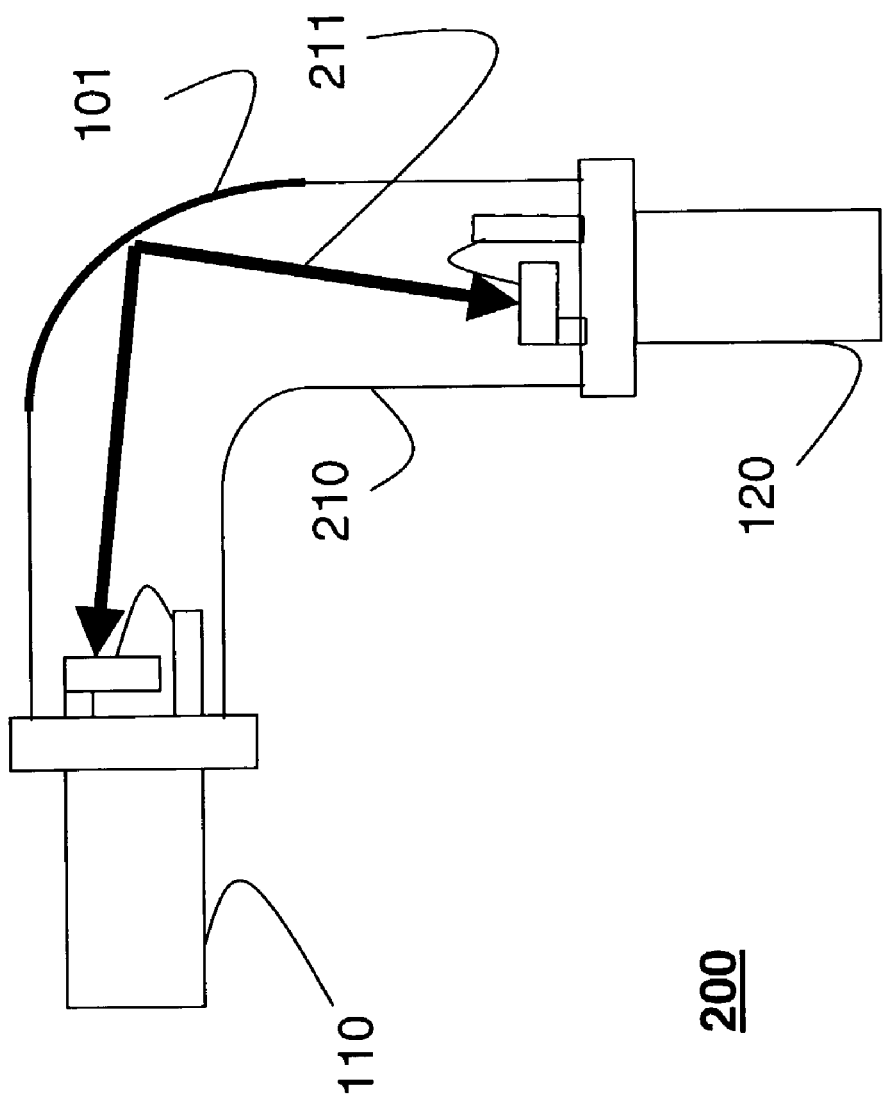
FIG. 2 is a side view of a two LED chemochromic sensor according to the invention.

FIG. 2 shows an arrangement 200 of a two-LED chemochromic sensor. The two LEDs 110 and 120 are at right angles to each other. The LEDs are connected by a transparent, elbow-shaped light-guide 210. The mixture is applied to the test area 101 at the corner of the light-guide 210 where light 211, in either direction, is reflected.

Figure 3:
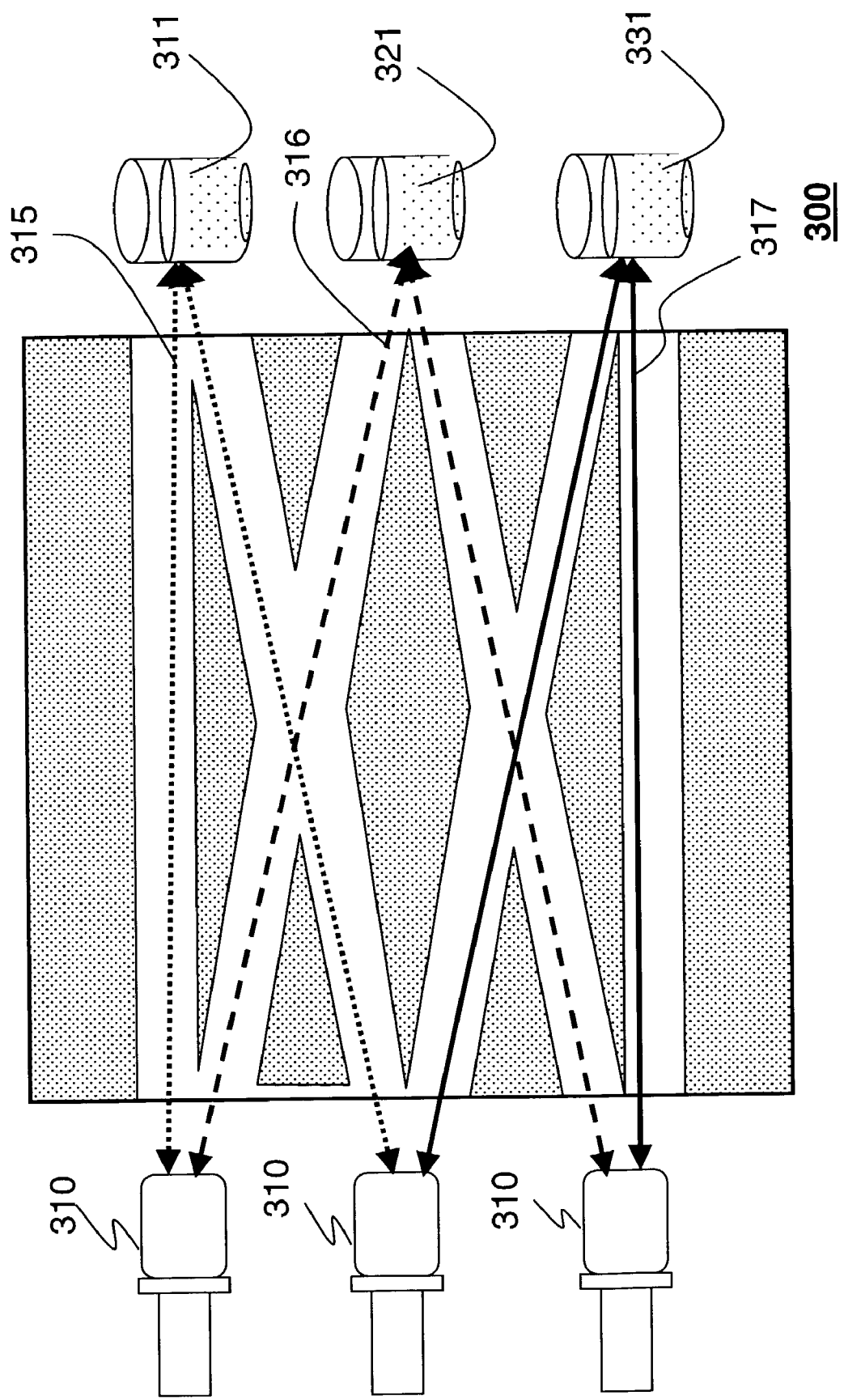
FIG. 3 is a side view of a three LED chemochromic sensor according to the invention.

FIG. 3 shows a chemochromic sensor 300 with multiple LEDs 310 and multiple light-guides 315–317. For calibration purposes, some of the light-guides are used for measuring known amounts of test material, while other-light guides are used for measuring unknown amounts of test material. Multiple light-guides provide higher accuracy, repeatability, and shorter testing times. For example, light-guide 315 is used to measure only a chemochromic reagent 311 for aging characteristics, light-guide 316 is used to measure a known amount of test material 321, and light-guide 317 is used to measure an unknown amount of test material 331. It should be noted that additional sensors and light-guides can be used.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

We claim:

1. A chemochromic sensor comprising:
   a microprocessor including a first pair of I/O pins and a second pair of I/O pins, and means for measuring a voltage drop across the first pair of I/O pins and the second pairs of I/O pins;
   a first light-emitting diode connected to the first pair of I/O pins;
   a second light-emitting diode connected to the second pair of I/O pins;
   a test area configured to receive a mixture of a chemochromic reagent and a test material; and
   means for driving the first light-emitting diode in forward bias to emit light onto the test area while driving the second light-emitting diode in reverse bias to sense light from the test area by measuring the voltage drop across the second pair of I/O pins to measure a first amount of the test material.

2. The sensor of claim 1 further comprising:
   means for driving the second light-emitting diode in forward bias to emit light onto the test area while driving the first light-emitting diode in reverse bias to sense light from the test area by measuring the voltage drop across the first pair of I/O pins to measure a second amount of the test material; and means comparing the first and second amounts to differentially measure the test material.

3. The chemochromic sensor according to claim 1 wherein the test area is located on a light-guide optically coupling the first and second light-emitting diodes.

4. The chemochromic sensor according to claim 3 wherein the first and second light-emitting diodes are at right angles to each other and the light-guide is elbow-shaped.

5. The chemochromic sensor according to claim 3 wherein the test area is at a corner of the light-guide.

6. The chemochromic sensor according to claim 1 wherein the voltage drop is measured by a timer of the microprocessor.

7. A method for sensing a chemochromic reagent and test material comprising:

driving a first light-emitting diode, having a first pair of I/O pins, in forward bias to emit light onto a test area containing a mixture of the chemochromic reagent and the test material; and driving a second light-emitting diode, having a second pair of I/O pins, in reverse bias to sense light from the test area by measuring a voltage drop across the second pair of I/O pins to measure a first amount of test material.

8. The method of claim 7 further comprising:

driving the second light-emitting diode in forward bias to emit light onto the test area containing a mixture of the chemochromic reagent and the test material; and driving the first light-emitting diode in reverse bias to sense light from the test area by measuring the voltage drop across the first pair of I/O pins to differentially measure a second amount of the test material; and comparing the first and second amounts to differentially measure the test material.

9. A chemochromic sensor comprising:

a microprocessor including a plurality of pairs of I/O pins and means for measuring a voltage drop across each pair of I/O pins;

a plurality of light-emitting diodes, one light emitting diode connected to one pair of I/O pins;

a plurality of test areas each configured to receive chemochromic materials; and means for driving a particular light-emitting diode in forward bias to emit light onto selected test areas while driving other ones of the light-emitting diodes in reverse bias to sense light reflected from the selected test areas by measuring the voltage drop across corresponding pairs of I/O pins of the reverse driven light emitting diodes, the voltage drops corresponding to amounts of the chemochromic materials.

* * * * *